United States Patent [19]

Coy et al.

[11] Patent Number: 4,508,711

[45] Date of Patent: Apr. 2, 1985

[54] CYCLIC PENTAPEPTIDE DISPLAYING SOMATOSTATIN ANTAGONISM AND METHOD OF TREATMENT OF MAMMALS THEREWITH

[75] Inventors: David H. Coy, New Orleans; William A. Murphy, Slidell, both of La.

[73] Assignee: American Cyanamid Company, Stamford, Conn.

[21] Appl. No.: 578,921

[22] Filed: Feb. 10, 1984

Related U.S. Application Data

[63] Continuation of Ser. No. 485,770, Apr. 18, 1983, abandoned.

[51] Int. Cl.[3] .................... A61K 37/00; C07C 103/52
[52] U.S. Cl. ................................. 514/11; 260/112.5 S
[58] Field of Search .................. 260/112.5 S; 424/177

[56] References Cited

U.S. PATENT DOCUMENTS

| 4,146,612 | 3/1979 | Veber | 260/112.5 S |
| 4,310,518 | 1/1982 | Freidinger et al. | 260/112.5 S |
| 4,360,516 | 11/1982 | Freidinger et al. | |
| 4,374,060 | 2/1983 | Nutt | 260/112.5 S |

Primary Examiner—Delbert R. Phillips
Attorney, Agent, or Firm—Estelle J. Tsevdos; Alphonse R. Noë

[57] ABSTRACT

Novel cyclic pentapeptide somatostatin antagonist and method for increasing the release of growth hormone, insulin, and glucagon in mammals are described.

8 Claims, No Drawings

CYCLIC PENTAPEPTIDE DISPLAYING SOMATOSTATIN ANTAGONISM AND METHOD OF TREATMENT OF MAMMALS THEREWITH

This is a continuation of application Ser. No. 485,770, filed Apr. 18, 1983, now abandoned.

The invention herein described relates to a novel cyclic pentapeptide somatostatin antagonist and method for increasing the release of growth hormone, insulin, and glucagon in mammals therewith.

Mammalian somatostatin, which has the following tetradecapeptide sequence:

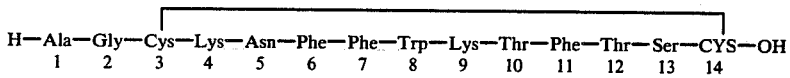

This hormone inhibits the release of growth hormone from the pituitary and insulin and glucagon from the pancreatic islet cells. It also has inhibitory actions on numerous other endocrine and gastrointestinal activities in mammals. These inhibitory effects are well documented (c. f., P. Brazeau et al., Science 179: 77–79, (1973); W. A. Mortimer et al., Lancet 1: 697–701, (1974), and C. A. Meyers et al. in Gastrointestinal Hormones, edited by G. B. L. Glass. Raven Press, New York, 1980, pages 363–385), and their importance to the life cycle of mammals is clearly recognized.

It is not, therefore, surprising to find that hundreds of somatostatin analogs have been synthesized and evaluated in an attempt to find agonists and antagonists or competitive inhibitors of said hormone. However, heretofore, no entirely satisfactory somatostatin antagonist or competitive inhibitor of this hormone has been available or disclosed in the art. The availability of a somatostatin antagonist should help to elucidate the known functions of the hormone in controlling multiple physiological effects.

It is, therefore, an object of the present invention to provide a novel somatostatin antagonist effective for increasing release of growth hormone, insulin, and glucagon in mammals. This object is manifest in the following description and particularly delineated in the appended claims.

Surprisingly, this objective was achieved during an attempted synthesis of cyclo(7-aminoheptanoyl-Phe-D-Trp-Lys-Thr), when catalytic hydrogenation of the protected peptide intermediate unexpectedly yielded the highly effective somatostatin antagonist, cyclo[7-aminoheptanoyl-Phe-D-Trp-Lys-Thr(Bzl)], in which the benzyl protecting group on Thr could not be removed even upon prolonged treatment under standard conditions.

The novel somatostatin antagonist of this invention is a cyclic pentapeptide depicted by the structural formula (I) and the pharmaceutically acceptable salts thereof, having the following amino acid sequence:

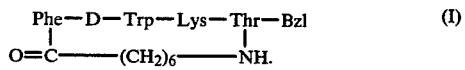

This compound may be described in abbreviated form as: cyclo[7-aminoheptanoyl-Phe-D-Trp-Lys-Thr(Bzl)] wherein Phe is phenylalanyl; D-Trp is D-tryptophyl; Lys is lysyl; Thr is threonyl, and Bzl is benzyl.

The term "pharmaceutically acceptable salts," as used in the present specification, is intended to mean non-toxic acid addition salts which are commonly used in the pharmaceutical industry. Among those of particular interest in the present invention are the hydrochloride, phosphate, sulfate, laurate, citrate, gluconate, succinate, acetate, and oleate salts of the formula (I) compounds. These salts are readily prepared by methods well known in the art.

In keeping with standard nomenclature, abbreviations used in the present specification and claims are as follows:

| | |
|---|---|
| Bzl = | benzyl |
| FMOC = | fluorenylmethyloxycarbonyl |
| Boc = | t-butyloxycarbonyl |
| HPLC = | high performance liquid chromatography |
| TFA = | trifluoroacetic acid |
| TLC = | thin-layer chromatography |
| Ahep = | 7-aminoheptanoyl |
| Cl—Z = | 4-chlorobenzyloxycarbonyl |

As will hereinafter be shown, injection of formula (I) peptide into rats completely blocks the inhibitory effects of exogenous somatostatin on growth hormone, insulin, and glucagon release. It will also be seen that in fasted rats, basal hepatic portal insulin and glucagon levels are significantly increased after treatment with cyclo[Ahep-Phe-D-Trp-Lys-Thr(Bzl)]; and, further, that plasma growth hormone levels in NEMBUTAL®-anesthetized and stimulated rats are increased after injection with the above-said compound. NEMBUTAL® sodium pentobarbital is a product of Abbott Laboratories.

The following examples further illustrate the present invention.

Solid-phase synthesis of the formula (I) peptide can be carried out on a Beckman 990 automatic peptide synthesizer. Preparative HPLC can be performed on a thick-walled glass column (2.5×45 cm) containing Whatman LRP-1 reverse phase packing ($C_{18}$ silica 13–20 μm) pumped with Fluid Metering Company pump and pulse damper. Amino acid analyses can be run on a Beckman 119 CL analyzer and processed with a System AA computing integrator.

Amino acid derivatives utilized in the preparation of the compounds of the present invention are available from several chemical supply houses including: Bachem, Inc., Torrance, Calif., and Chemical Dynamics, Inc., Plainfield, N.J.

Conveniently, the formula (I) peptide of this invention can be prepared beginning with the appropriate α-amino protected amino acid coupled to an appropriate resin, such as a polystyrene resin with 1–2 percent by weight of divinyl benzene as a cross-linking agent.

Protecting groups for the amino acids include: t-butyloxycarbonyl, isopropyloxycarbonyl, diisopropyloxycarbonyl, benzyloxycarbonyl, cyclopentyloxycarbonyl, and the like; but, t-butyloxycarbonyl or isopropyloxycarbonyl are generally preferred.

In the process, FMOC-Lys-(Boc)-Thr(Bzl)-Ahep-Phe-D-Trp-O-Ch₂-resin is prepared beginning with the appropriate Boc-D-Trp-Merrifield resin. The resin is placed in the reaction vessel of the peptide synthesizer which has been programmed to carry out the following work-wash cycle: (a) methylenechloride, (b) 33% TFA in methylene chloride, (c) methylene chloride, (d) ethyl alcohol, (e) methylene chloride, (f) 10% triethylamine in methylene chloride, and (g) methylene chloride.

The washed resin with the Boc group removed is then stirred with t-Boc-Phe and diisopropylcarbodiimide in methylene chloride. The protected attached amino acid is then cycled through steps (b) through (g) in the above wash program. Thereafter, the following amino acids are coupled by the same cycle of events: t-Boc-Ahep, t-Boc-Thr(Bzl) and FMOC-Lys(Boc), wherein Bzl is benzyl. These steps provide the FMOC-Lys(Boc)-Thr(Bzl)-Ahep-Phe-D-Trp-O-CH₂-Resin.
Removal of the protected peptide from the resin by treatment with a ten-fold excess of hydrazine in methanol is accompanied by loss of the base-sensitive FMOC group to give H-Lys(Boc)-Thr(Bzl)-Ahep-Phe-D-Trp-NHNH₂, which is cyclized with hydrochloric acid and isoamylnitrite to give cyclo[Ahep-Phe-D-Trp-Lys(-Boc)-Thr(Bzl)]. Treatment of this peptide with 90% TFA in water containing 1% ethanedithiol then yields the desired somatostatin antagonist of this invention cyclo[Ahep-Phe-D-Trp-Lys-Thr(Bzl)]. These reactions are graphically illustrated in the Flow Diagram I below:

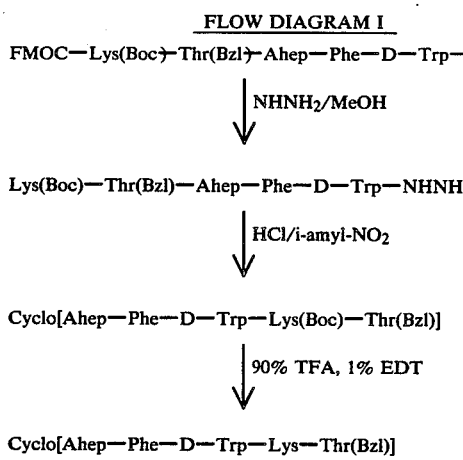

As indicated above, the somatostatin antagonist of the present invention was unexpectedly prepared during the preparation of cyclo(Ahep-Phe-D-Trp-Lys-Thr), a somatostatin analog essentially devoid of somatostatin antagonist activity.

After conventional solid-phase assembly beginning with 1 mmole of Boc-Phe-Merrifield resin (1% cross-linked), the protected peptide hydrazide, [D-Trp-Lys(Cl-Z)-Thr(Bzl)-Ahep-Phe-NHNH₂ was cleaved from the support by treatment with hydrazine in methanol and isolated by a procedure described by D. F. Veber et al., *Proceedings of the National Academy of Science*, U.S.A., 75: 2636–2640, (1978). Without further purification, the hydrazide was converted to the azide, neutralized with triethylamine, and cyclized in DMF solution. The crude ninhydrin negative material was deprotected by treatment with HF-anisole under standard conditions, as described by G. T. Engberg et al., *Nature*, 293: 222-223, (1981), and purified by preparative HPLC eluting with 10–55% gradient of CH₃CN in 20% AcOH.

The pure peptide, cyclo(Ahep-Phe-D-Trp-Lys-Thr), which has little or no somatostatin antagonist activity, was obtained in 15% overall yield. This compound gave one Cl-starch, ninhydrin, and Ehrlich reagent positive spot with the following R$_f$'s on silica gel TLC plates: N-BuOH:AcOH:H₂O:EtOAc (1:1:1:1), 0.64; N-BuOH:AcOH:H₂O (4:1:1), 0.47; EtOAc:-Pyridine:AcOH:H₂O (5:5:1:3), 0.73; i-PrOH:1M AcOH (2:1), 0.63. Amino acid analysis of a sample hydrolyzed in methanesulfonic acid containing 0.1% tryptamine gave: Thr, 1.05; Phe, 1.00; Lys, 1.01, and Trp, 0.82.

When the protected cyclo[Ahep-Phe-D-Trp-Lys-(Cl-Z)-Thr(Bzl)] was hydrogenated at atmospheric pressure and room temperature over 10% Pd on charcoal, a single major product was formed which was faster moving in the 4-TLC solvent systems. It had identical physio-chemical properties to cyclo[Ahep-Phe-D-Trp-Lys-Thr(Bzl)], the somatostatin antagonist of this invention. HF treatment of this material converted it to a peptide behaving identically to cyclo(Ahep-Phe-D-Trp-Lys-Thr), a peptide which has little or no somatostatin antagonist activity. The above reactions are graphically illustrated in Flow Diagram II below.

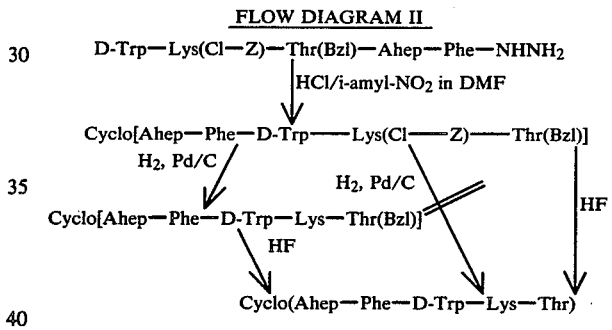

The compound of formula (I) is useful as a somatostatin antagonist and is effective for increasing the release of growth hormone, insulin, and glucagon, in mammalian hosts, when administered thereto at dosages of from 0.000002 to 1 mg/kg of mammalian body weight per day.

The formula (I) compound may be administered orally in the form of a feed additive or as a bolus, pill, tablet, oral gel, or the like, designed to deliver the active compound at the dosage level desired. It may also be administered parenterally by intramuscular, subcutaneous, intraperitoneal or intravenous injection, or as a transdermal or nasal spray.

EXAMPLE 1

Preparation of
N$^{\alpha}$9-Fluorenylmethyloxycarbonyl-N$^{\epsilon}$-tert-butyloxycarbonyl-L-lysyl-O-benzyl-L-threonyl-7-aminoheptanoyl-L-phenylalanyl-D-tryptophyl-O-CH₂ resin t-Butyloxycarbonyl-D-tryptophyl-Merrifield resin (1% cross-linked, 1.25 g 0.5 mmol) is placed in the reaction vessel of a Beckman Model 990 automatic peptide synthesizer programmed to carry out the following work-wash cycle: (a) CH₂Cl₂; (b) 33% trifluoroacetic acid in CH₂Cl₂ (2 times for 1 and 25 minutes each); (c) CH₂Cl₂; (d) C₂H₅OH; (e) CH₂Cl₂; (f) 10% (CH₂H₅)₃N in CH₂Cl₂ (2 times for 2 minutes each); and (g) CH₂Cl₂.

The washed resin with the t-butyloxycarbonyl (Boc) group removed is stirred with t-butyloxycarbonyl-L-phenylalanine (t-Boc-Phe) and diisopropylcarbodiimide (3 mmol) in $CH_2Cl_2$ for one hour, and the resulting amino acid resin then washed with $CH_2Cl_2$. The protected, attached amino acids are then cycled through steps (b) through (g) in the above wash program. The following amino acids (3 mmol) are then coupled successively by the same treatment cycle: t-butyloxycarbonyl-7-aminoheptanoyl (t-Boc-Ahep); t-Boc-Thr(Bzl) and fluorenylmethyloxycarbonyl-lysyl-t-butyloxycarbonyl [FMOC-Lys(Boc)].

Upon completion of the last coupling reaction, the resulting resin is washed with methanol to obtain the above-identified resinated product.

EXAMPLE 2

Preparation of
$N^\epsilon$-tert-Butyloxycarbonyl-L-lysyl-O-benzyl-L-threonyl-7-aminoheptanoyl-L-phenylalanyl-D-tryptophyl-$NHNH_2$ $N^{\alpha 9}$-Fluorenylmethyloxycarbonyl-$N^\epsilon$-tert-butyloxycarbonyl-L-lysyl-O-benzyl-L-threonyl-7-aminoheptanoyl-L-phenylalanyl-D-tryptophyl-O-$CH_2$ resin (1.7 g, 0.5 mmol) is suspended in 70 mL of dry methanol and the thus prepared suspension then treated with 7 mL of anhydrous hydrazine. The mixture is stirred for 24 hours at ambient temperature and then filtered, washed with methanol and the methanol extracts evaporated to yield an oily residue that solidified upon trituration with ether to give 0.50 g of the above-named product in the form of an off-white powder.

EXAMPLE 3

Preparation of
Cyclo(7-aminoheptanoyl)-L-phenylalanyl-D-tryptophyl-$N^\epsilon$-tert-butyloxycarbonyl-L-lysyl-O-benzyl-L-threonyl)

The peptide hydrazide $N^\epsilon$-tert-butyloxycarbonyl-L-lysyl-O-benzyl-L-threonyl-7-aminoheptanoyl-L-phenylalanyl-D-tryptophyl-$NHNH_2$ (0.5 g, 0.5 mmol) is dissolved in 10 mL of dimethylformamide (DMF) and cooled to $-35°$ C. The solution is then acidified to pH 1.5 with hydrochloric acid in tetrahydrofuran (HCl/THF) and isoamylnitrite (67 µL). The mixture is stirred at $-35°$ C. for 45 minutes and then added to 1.5 mL of dimethylformamide (DMF) cooled to $-25°$ C. The reaction mixture is then neutralized to pH 7.5 with diisopropylethylamine and maintained at $-25°$ C. for 24 hours and 5° C. for an additional 24 hours. Evaporation of the DMF gives the above-identified product as a dark oil that exhibits a major spot by thin-layer chromatography (tlc).

EXAMPLE 4

Preparation of
Cyclo(7-aminoheptanoyl-L-phenylalanyl-D-tryptophyl-L-lysyl-O-benzyl-L-threonyl)

The fully protected peptide cyclo (7-aminoheptanoyl-L-phenylalanyl-D-tryptophyl-$N^\epsilon$-tert-butyloxycarbonyl-L-lysyl-O-benzyl-L-threonyl) is dissolved in 50 mL of a mixture of 90% trifluoroacetic acid (TFA), water and 1,2-ethanedithiol, prepared in a ratio of 45:4.5:0.5 by volume. The solution is stirred at ambient temperature for 40 minutes and then evaporated to an oil. The resulting oil is purified by high performance liquid chromatography to give the above-named product in 33% yield. One spot is obtained in the 4 TLC solvent systems with the following $R_f$'s: n-BuOH:AcOH:$H_2O$:EtOAc(1:1:1:1), 0.72; n-BuOH:AcOH:$H_2O$(4:1:1), 0.58; EtOAc:pyridine:AcOH:$H_2O$(5:5:1:3), 0.81; i-PrOH:1M AcOH(2:1), 0.67. Amino acid analysis gives Thr, 0.98; Phe, 1.00; Lys, 0.98 and Trp, 1.02.

EXAMPLE 5

Evaluation of peptide effects on growth hormone, insulin and glucagon release in mammals using the rat as the test species In this evaluation the procedures described by W. A. Murphy et al. Endocrinology 109:491-495 (1980), were employed.

In growth hormone (GH) experiments, male rats (Charles Rivers) were anesthetized with NEMBUTAL ® (5 mg per 100 g/BW) which also served to maintain stimulated plasma GH levels. Exactly 30 minutes after the rats were anesthetized, 0.5 mL of saline or the test peptide in saline was administered as a sc bolus. A 1 mL blood sample was drawn from the jugular vein 15 minutes after the injection. For examining blocking effects of the analog on somatostatin, the cyclic peptide was given 5 minutes prior to somatostatin. GH levels were determined using NIADDKD rat GH RIA components.

For measurement of effects on insulin and glucagon levels, rats were fasted 27-30 hours and anesthetized with NEMBUTAL ® (5 mg per 100 g body wt). Exactly 21 minutes after NEMBUTAL ® injection 0.5 mL of saline or saline containing test peptide was injected into the jugular vein over a 1 minute period. Five minutes later, 3.5 mL of blood were quickly drawn from the hepatic portal vein after rapid laparotomy. Blocking effects of analog on exogenous somatostatin were examined by simultaneous injection of both peptides. Plasma insulin levels were determined using matched insulin RIA kits purchased from Cambridge Nuclear, Billerica, MA. Plasma glucagon was determined using Unger 30K antibody and $^{125}I$-glucagon (Cambridge Nuclear) as the tracer. Data obtained are reported in Tables I, II and III below.

In these tests, cyclo[7-aminoheptanoyl-Phe-D-Trp-Lys-Thr(Bzl)] is the pentapeptide of the present invention and is referred to as CPP-1 in Tables I and III. The compound referred to as CPP-2 is cyclo(7-aminoheptanoyl-Phe-D-Trp-Lys-Phe), a close relative of CPP-1 but is devoid of the Thr(Bzl) function.

From the tables, it can be seen that the effects of both CPP-1, the compound of this invention and CPP-2 on NEMBUTAL ®-simulated GH release in rats were measured. Radioimmunoassayable GH levels in control-simulated jugular blood of 277±40 ng/mL rose significantly to 547±65 ng/mL after injection of 0.6 µg/100 g body wt of the Thr(Bzl) analog (Table I). Thus this peptide, rather then being the expected weak somatostatin agonist, was apparently blocking endogenous somatostatin resulting in actual release of GH. Indeed, the normal suppressive effect on GH levels of synthetic somatostatin (Experiment 1 of Table I) could be eliminated by prior injection of the analog (Experiment 2 of Table I). In contrast cyclo(Ahep-Phe-D-Trp-Lys-Phe) (Table I) was devoid of any effects on GH release.

A more complete dose response of the Thr(Bzl) peptide effects on GH release (Table II) revealed that 0.6 and 1.2 µg dose levels produce maximum stimulation.

Higher doses of 2.4 and 4.8μ did not significantly increase GH levels. This biphasic effect would indicate that the analog retains partial agonist activity which becomes apparent at higher doses.

Inhibitory properties of endogenous and synthetic somatostatin on rat hepatic portal insulin and glucagon levels could also be eliminated by injection of the Thr(Bzl) pentapeptide (Table III). In fasted rats, a basal insulin concentration of 67±11/μU ml rose to what appeared to be maximally stimulated levels of 104±7 and 112±21 μU/ml five minutes after injection. Even higher doses of 1 and 5 μg 100 g/body wt of the analog (Table III, Experiment 2) increased glucagon from 45±3 to 108±77 and 147±20 pg/ml, respectively, in a dose-dependent manner. When the antagonist and somatostatin were both injected together, the antagonist counteracted the inhibitory effects of somatostatin to bring the hormone levels back to or, in the second experiment, above control values.

From the above data, it appears that the antagonist effect of the compound of the present invention is dependent on the presence of the aromatic benzyl protecting group on the threonine.

TABLE I

Effects of the cyclic pentapedtides, Cyclo-[7-aminoheptanoyl-Phe—D-Trp—Lys—Thr(Bzl)] (CPP-1) and Cyclo(7-aminoheptanoyl-Phe—D-Trp—Lys—Phe) (CPP-2), compared to somatostatin on GH levels in the rat (5 animals per group)

| Peptide | Dose (μg/100 g body weight) | GH (ng/mL)* |
|---|---|---|
| Experiment 1 | | |
| Saline | — | 277 ± 40 |
| Somatostatin | 0.2 | 146 ± 14 |
| | 0.6 | 78 ± 26 |
| CPP-1 | 0.2 | 357 ± 54 |
| | 0.6 | 547 ± 65+ |
| CPP-2 | 0.2 | 224 ± 68 |
| | 0.6 | 302 ± 61 |
| Experiment 2 | | |
| Saline | — | 403 ± 85 |
| Somatostatin | 0.4 | 107 ± 13 |
| Somatostatin + CCP-1 | 0.4 + 2.0 | 393 ± 125§ |
| | 0.4 + 10.0 | 296 ± 61 |

Fed rats were used in the first experiment and fasted rats in the second.
* = Mean ± standard error.
+ = p < 0.01 vs saline.
± = p < 0.05 vs saline.
§ = p < 0.05 vs somatostatin (0.4 μg); NS vs saline.

TABLE II

Dose-dependent effects of Cyclo [Ahep—Phe—D-Trp—Lys—Thr(Bzl)] on GH release in anesthetized rats (4–6 animals per group)

| Dose (μg 100 g BW) | GH(ng/mL) (Mean ± SE) |
|---|---|
| Saline | 637 ± 68 |
| 0.3 | 801 ± 67 |
| 0.6 | 1160 ± 162° |
| 1.2 | 1070 ± 119* |
| 2.4 | 804 ± 114 |
| 4.8 | 732 ± 220 |

* = p < 0.05 vs saline.

TABLE III

Effect of The(Bzl) somatostatin antagonist (CPP-1) compared to somatostatin and saline on insulin and glucagon levels in hepatic portal blood of fasted rats (5 animals per group)

| Peptide | Dose (μg/100 g) | Insulin (μU/mL) (Mean ± SE) | Glucagon (pg/mL) (Mean ± SE) |
|---|---|---|---|
| Experiment 1 | | | |
| Saline | — | 67 ± 11 | 80 ± 5 |
| Somatostatin | 0.4 | 57 ± 3 | 64 ± 3 |
| | 2.0 | 28 ± 11 | 46 ± 4 |
| CPP-1 | 0.8 | 104 ± 7+ | 79 ± 8 |
| | 4.0 | 112 ± 21+ | 114 ± 14* |
| Saline | — | 46 ± 5 | 94 ± 9 |
| Somatostatin | 1.0 | 11 ± 2 | 78 ± 7 |
| Somatostatin + CPP-1 | 1.0 + 2.0 | 41 ± 6 | 119 ± 8+ |
| Experiment 2 | | | |
| Saline | — | — | 45 ± 3 |
| Somatostatin | 1.0 | — | 18 ± 7 |
| CPP-1 | 1.0 | — | 108 ± 17+ |
| | 5.0 | — | 147 ± 20* |
| Somatostatin + CPP-1 | 1.0 + 1.0 | — | 104 ± 27+ |

* = p < 0.01 vs saline.
+ = p < 0.05 vs saline.
= p < 0.01 vs SS.

What is claimed is:

1. A cyclic pentapeptide compound having the structure:

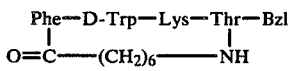

or a pharmaceutically acceptable salt thereof.

2. A compound according to claim 1, Cyclo-[Ahep-Phe-D-Trp-Lys-Thr(Bzl)].

3. A method for increasing the release of growth hormone in mammals comprising administering thereto from 0.00001 to 1 mg/kg of mammalian body weight/day of a compound having the structure:

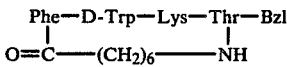

or a pharmaceutically acceptable salt thereof.

4. A method for increasing the release of insulin in mammals comprising administering thereto from 0.00001 to 1 mg/kg of mammalian body weight/day of a compound having the structure:

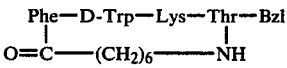

or a pharmaceutically acceptable salt thereof.

5. A method for increasing the release of glucagon in mammals comprising administering thereto from 0.00001 to 1 mg/kg of mammalian body weight/day of a compound having the structure:

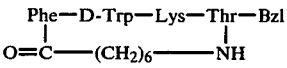

or a pharmaceutically acceptable salt thereof.

6. A method according to claim 3 for releasing growth hormone in mammals wherein the compound administered to said mammalian host is Cyclo[Ahep-Phe-D-Trp-Lys-Thr(Bzl)].

7. A method according to claim 4 for releasing insulin in mammals wherein the compound administered to said mammalian host is Cyclo[Ahep-Phe-D-Trp-Lys-Thr(Bzl)].

8. A method according to claim 5 for releasing glucagon in mammals wherein the compound administered to said mammalian host is Cyclo[Ahep-Phe-D-Trp-Lys-Thr(Bzl)].

* * * * *